United States Patent vonBebenburg et al.

[11] 4,009,271
[45] * Feb. 22, 1977

[54] 6-AZA-3H-1,4-BENZODIAZEPINES

[75] Inventors: Walter vonBebenburg, Buchschlag; Heribert Offermanns, Grossauheim, both of Germany

[73] Assignee: Deutsche Gold- und Silber-Scheideanstalt vormals Roessler, Frankfurt, Germany

[ * ] Notice: The portion of the term of this patent subsequent to Feb. 1, 1989, has been disclaimed.

[22] Filed: June 25, 1975

[21] Appl. No.: 590,285

Related U.S. Application Data

[63] Continuation-in-part of Ser. No. 460,525, April 12, 1974, Pat. No. 3,941,775.

[52] U.S. Cl. .................. 424/248.57; 260/247.1 E; 260/247.2 R; 260/247.5 GP; 260/256.4 F; 260/268 BC; 260/293.59; 260/294.8 R; 260/294.9; 260/295 R; 260/295 F; 260/295 S; 260/296 H; 260/297 R; 260/239.3 B; 424/250; 424/263; 424/267; 424/248.56

[51] Int. Cl.² .............. C07D 471/04; A61K 31/44

[58] Field of Search ......... 260/239.3, 247.2, 247.5, 260/295, 296, 293.59, 268, 294.8 R, 294.9, 247.1 E; 424/244, 248, 263, 267, 250

[56] References Cited

UNITED STATES PATENTS 3,920,633  11/1975  von Bebenburg et al. ... 260/239.3 B
3,941,775  3/1976   von Bebenburg et al. .... 260/296 R Primary Examiner—Natalie Trousof
Assistant Examiner—R. W. Ramsuer
Attorney, Agent, or Firm—Cushman, Darby & Cushman

[57] ABSTRACT

There are produced 6-aza-3H-1,4-benzodiazepines and 6-aza-1,2-dihydro-3H-1,4-benzodiazepines of the formula:

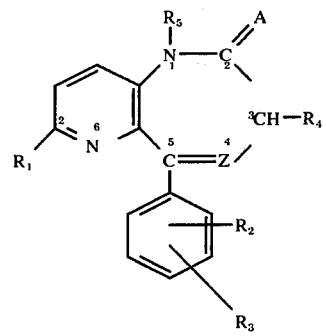

wherein
$R_1$ is the group $-NR_aR_b$ or $-NR_aR_bR_c$ halide and $R_a$ and $R_b$ are the same or different and are hydrogen, alkyl groups of 1 to 6 carbon atoms, or alkyl groups of 1 to 6 carbon atoms substituted by hydroxy, phenyl or a carboxy group, and $R_c$ can be as defined for $R_a$ and $R_b$ except it cannot be hydrogen and wherein the group $-NR_aR_b$ also can be a saturated closed 5, 6 or 7 membered ring which in a given case has a further oxygen atom or nitrogen atom or contains a nitrogen atom substituted with an alkyl group having 1 to 4 carbon atoms;
$R_2$ and $R_3$ are the same or different and are hydrogen, halogen, trifluoromethyl, nitro, nitrile, hydroxy, lower alkyl or lower alkoxy;
$R_4$ is hydrogen;
Z is a nitrogen atom or the NO group;
$R_5$ is hydrogen, lower alkyl, lower alkenyl, aminoalkyl of 2 to 4 carbon atoms, mono or di lower alkyl substituted aminoalkyl of 2 to 4 carbon atoms; and
A is oxygen, and the $-N(R_5)-C-(=A)-$ can also be in the tautomeric form $-N=C(AR_5)-$, pharmacologically acceptable salts and quaternary ammonium and alkyl ammonium compounds thereof. The compounds have pharmacodynamic properties including psychosedative and anxiolytic properties as well as antiphlogistic properties.

12 Claims, No Drawings

6-AZA-3H-1,4-BENZODIAZEPINES

This application is a continuation-in-part of application Ser. No. 460,525 filed Apr. 12, 1974 now U.S. Pat. No. 3,941,775.

The present invention is concerned with new 6-aza-3H-1,4-benzodiazepines and 6-aza-1,2-dihydro-3H-1,4-benzodiazepines of the formula:

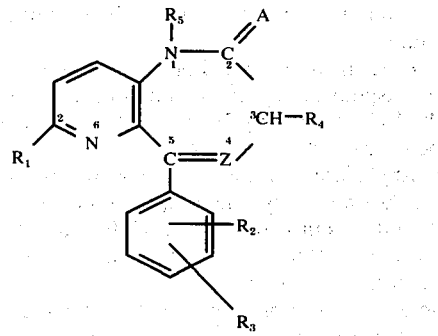

wherein $R_1$ is the group $-NR_aR_b$, $N^+R_aR_bR_cX^-$ where $X^-$ is a halide, sulfate, acetate, citrate or p-toluene sulfonate and $R_a$ and $R_b$ are the same or different and are hydrogen, alkyl groups of 1 to 6 carbon atoms, or alkyl groups of 1 to 6 carbon atoms substituted by hydroxy, phenyl or a carboxy group, and $R_c$ can be defined as for $R_a$ and $R_b$ except it cannot be hydrogen and wherein the group $-NR_aR_b$ also can be a saturated closed 5, 6 or 7 membered ring which in a given case has a further oxygen atom or nitrogen atom or contains a nitrogen atom substituted with an alkyl group having 1 to 4 carbon atoms;

$R_2$ and $R_3$ are the same or different and are hydrogen, halogen, trifluoromethyl, nitro, nitrile, hydroxy, lower alkyl or lower alkoxy;

$R_4$ is hydrogen;

Z is a nitrogen atom or the NO group;

$R_5$ is hydrogen, lower alkyl, lower alkenyl, aminoalkyl of 2 to 4 carbon atoms, mono or di lower alkyl substituted aminoalkyl of 2 to 4 carbon atoms; and A is oxygen, and the $-N(R_5)-C-(=A)-$ can also be in the tautomeric form $-N=C(AR_5)-$, pharmacologically acceptable salts and quaternary ammonium and alkyl ammonium compounds thereof. The compounds have pharmacodynamic properties including psychosedative and anxiolytic properties as well as antiphlogistic properties.

In the compounds of formula I the halogen atoms can have an atomic weight of 9 to 80, i.e., they can be chlorine, fluorine or bromine, preferably chlorine and fluorine. As the above named lower alkyl, alkenyl, alkoxy and hydroxyalkyl groups there can be employed those containing 1 to 6 carbon atoms, preferably 1 to 4 carbon atoms. The aminoalkyl group can contain 2 to 4 carbon atoms and can be straight or branch chained. Preferably the aminoalkyl group contains 2 carbon atoms. The alkyl groups as such or as constituents of other groups can be either straight chain or branched. Examples of suitable groups are methyl, ethyl, propyl, isopropyl, butyl, tert. butyl, hexyl, isobutyl, methoxy, ethoxy, propoxy, isopropoxy, butoxy, isobutoxy, tert. butoxy, amyloxy, hexyloxy, hydroxymethyl, hydroxyethyl, hydroxypentyl, dimethylamino, diethylamino and dibutylamino.

In case $-NR_aR_b$ is closed to form a ring there is especially employed 6 or 7 membered rings which in a given case can contain an additional oxygen or nitrogen atom. For example, the group $-NR_aR_b$ form the morpholine ring, piperidine ring, piperazine ring or homopiperazine.

The quaternary compounds are such of those which contain the group $-NR_aR_bR_c$ wherein none of $R_a$, $R_b$ and $R_c$ is hydrogen. As anions for these quaternary compounds, there can be employed physiologically compatible anions of inorganic or organic acids, e.g., anions from sulfuric acid, hydrochloric acid, hydroiodic acid, hydrobromic acid, acetic acid, citric acid, p-toluene sulfonic acid or the other pharmaceutically compatible acids set forth below.

The compounds of the invention have valuable pharmacodynamic properties. For example, they have psychosedative and especially anxiolytic properties. Furthermore, there is also present an antiphlogistic effect.

In addition to the compounds mentioned in the working examples other compounds within the present invention includes:

5-phenyl-6-aza-7-diethylamino-1,2-dihydro-3H-1,4-benzodiazepinone-(2); 5-phenyl-6-aza-7-diisopropylamino-1,2-dihydro-3H-1,4-benzodiazepinone-(2); 5-phenyl-6-aza-7-dibutylamino-1,2-dihydro-3H-1,4-benzodiazepinone-(2);

5-phenyl-6-aza-7-dihexylamino-1,2-dihydro-3H-1,4-benzodiazepinone-(2);

5-phenyl-6-aza-7-hexylamino-1,2-dihydro-3H-1,4-benzodiazepinone-(2);

5-phenyl-6-aza-7-t-butylamino-1,2-dihydro-3H-1,4-benzodiazepinone-(2);

5-phenyl-6-aza-7-ethylamino-1,2-dihydro-3H-1,4-benzodiazepinone-(2);

5-phenyl-6-aza-7-amino-1,2-dihydro-3H-1,4-benzodiazepinone-(2);

5-phenyl-6-aza-7-piperidino-1,2-dihydro-dihydro-3H-1,4-benzodiazepinone-(2);

5-phenyl-6-aza-7-piperazino-1,2-dihydro-3H-1,4-benzodiazepinone-(2);

5-phenyl-6-aza-7-homopiperazino-1,2-dihydro-3H-1,4-benzodiazepinone-(2);

5-phenyl-6-aza-7-(3-hydropropylamino)-1,2-dihydro-3H-1,4-benzodiazepinone-(2);

5-phenyl-6-aza-7-(2-hydroxypropylamino)-1,2-dihydro-3H-1,4-benzodiazepinone-(2);

5-(o-trifluoromethylphenyl)-6-aza-7-dimethylamino-1,2-dihydro-3H-1,4-benzodiazepinone-(2);

5-(m-nitrophenyl)-6-aza-7-dipropylamino-1,2-dihydro-3H-1,4-benzodiazepinone-(2);

5-(o-hydroxyphenyl)-6-aza-7-methylamino-1,2-dihydro-3H-1,4-benzodiazepinone-(2);

5-(2',4'-dihydroxy-phenyl)-6-aza-7-morpholino-1,2-dihydro-3H-1,4-benzodiazepinone-(2);

5-(o-methylphenyl)-6-aza-7-sec. butylamino-1,2-dihydro-3H-1,4-benzodiazepinone-(2);

5-(2',4'-dimethylphenyl)-6-aza-7-diethylamino-1,2-dihydro-3H-1,4-benzodiazepinone-(2);

5-(p-methoxyphenyl)-6-aza-7-piperidino-1,2-dihydro-3H-1,4-benzodiazepinone-(2);

5-(p-hexylphenyl)-6-aza-7-amino-1,2-dihydro-3H-1,4-benzodiazepinone-(2);

1-aminoethyl-5-phenyl-6-aza-7-dimethylamino-1,2-dihydro-3H-1,4-benzodiazepinone-(2);

1-aminobutyl-5-(O-bromophenyl)-6-aza-7-(2-hydroxyethylamino)-1,2-dihydro-3H-1,4-benzodiazepinone-(2);

1-methylaminobutyl-5-phenyl-6-aza-7-dimethylamino-1,2-dihydro-3H-1,4-benzodiazepinone-(2);

5-(o-cyanophenyl)-6-aza-7-pyrrolidino-1,2-dihydro-3H-1,4-benzodiazepinone-(2);

5-(2'-chloro-4'-methylphenyl)-6-aza-7-dimethylamino-1,2-dihydro-3H-1,4-benzodiazepinone-(2);

5-phenyl-6-aza-7-dimethylamino-1,2-dihydro-3H-1,4-benzodiazepinone-(2)-4-oxide;

5-(p-methylphenyl)-6-aza-7-morpholino-1,2-dihydro-1,4-diazepinone(2);

5-(o-isopropylphenyl)-6-aza-7-ethylamino-1,2-dihydro-3H-1,4-benzodiazepinone-(2);

5-(o-chlorophenyl)-6-aza-7-propylamino-1,2-dihydro-3H-1,4-benzodiazepinone-(2);

5-(o-chlorophenyl)-6-aza-7-dimethylamino-1,2-dihydro-3H-1,4-benzodiazepinone-(2)-4-oxide;

5-(2',5'-dichlorophenyl)-6-aza-7-methylamino-1,2-dihydro-3H-1,4-benzodiazepinone-(2);

1-methyl-5-(o-fluorophenyl)-6-aza-7-benzylamino-1,2-dihydro-3H-1,4-benzodiazepinone-(2);

5-(o-fluorophenyl)-6-aza-7-dimethylamino-1,2-dihydro-3H-1,4-benzodiazepinone-(2);

1-methyl-5-phenyl-6-aza-7-dimethylamino-1,2-dihydro-3H-1,4-benzodiazepinone-(2);

1-allyl-5-phenyl-6-aza-7-methylamino-1,2-dihydro-3H-1,4-benzodiazepinone-(2);

1-butylaminoethyl-5-phenyl-6-aza-7-morpholino-1,2-dihydro-3H-1,4-benzodiazepinone-(2);

1-hexylaminopropyl-5-phenyl-6-aza-7-dimethylamino-1,2-dihydro-3H-1,4-benzodiazepinone-(2);

1-dimethylaminobutyl-5-phenyl-6-aza-7-morpholino-1,2-dihydro-3H-1,4-benzodiazepinone-(2);

1-dihexylaminoethyl-5-(o-chlorophenyl)-6-aza-7-isopropylamino-1,2-dihydro-3H-1,4-benzodiazepinone-(2);

The compounds can be prepared by methods which are known in themselves such as:

a. condensing a compound of the formula:

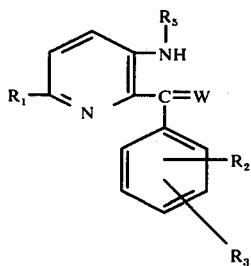

II where $R_1$, $R_2$, $R_3$ and $R_5$ are as defined above and W is an oxygen atom with a compound of the formula:

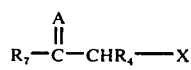

where $R_4$ is as defined above, A is oxygen and $R_7$ is a hydroxy group, a halogen atom (of atomic weight 9 to 80), a lower alkoxy group, a mercapto group, a lower alkylmercapto group, an amino group or a lower alkylamino group, the structural element $-C(=A)R_7$ collectively can also be a nitrile group and X is an amino group or a halogen atom, in a given case with addition of an acid binding agent, e.g., triethylamine, whereby it can be worked up in the presence of ammonia or an ammonium derivative; in the case where W is O and X is halogen and the reaction product is treated in a given case finally in an alkaline medium; or b. reacting a compound of formula I wherein $R_1$ is replaced by a halogen atom (preferably chlorine) and the remaining substituents have the meanings set forth above with compounds of the formula $HNR_aR_b$ or $NR_aR_bR_c$.

c. in a compound of formula I one or more of the symbols $R_1$, $R_5$, $R_4$, A and Z is changed into another compound corresponding to the definition of the formula.

Process (a) is carried out in the conventional solvents or suspension agents at temperatures between 0° and 200° C., preferably 20° to 150° C. Especially there can be employed polar solvents, for example alcohols, e.g., methyl alcohol, ethyl alcohol, isopropyl alcohol, propyl alcohol and butyl alcohol, dioxane, tetrahydrofurane, dimethyl sulfoxide, dimethyl formamide and similar materials. When W is O there can be used pyridine and quinoline. In a given case there are suitably added acidic or basic materials, as for example, piperidine or aliphatic carboxylic acids, e.g. acetic acid and propionic acid. When X is a halogen atom there are suitably employed basic materials which effect acid splitting, e.g. triethylamine. When $R_7$ is a hydroxy group (in this case the structural unit $-(=A)R_7$ for example, can make a carboxyl group) the addition of special customary water splitting off agents such as dicyclohexylcarbodiimide is suitable or in some cases necessary.

Frequently process (a) can also be carried out so that the amino group of formula III (X = NH$_2$) has a protective group. Frequently such protective groups are required for the production of the starting compounds.

In many cases the splitting off of such a protective group takes place simultaneously with the cyclization.

These protective groups are easily split off. There are employed either easily solvolytically splittable acyl groups or groups splittable by hydrogenation, as for example, the benzyl radical. The solvolytically splittable protective groups are split off for example, by saponification with dilute acids or by means of basic substances (potash, soda, aqueous alkali solutions, alcoholic alkali solutions, NH$_3$) at room temperature or with a short boiling. Hydrogenizably splittable groups such as the benzyl group or the carbobenzoxy radical are suitably split off by catalytic hydrogenation in the presence of customary hydrogenation catalysts, especially palladium catalysts, in a solvent or suspension agent, in a given case under elevated pressure. As solvents or suspensions agent there can be used water, lower aliphatic alcohols such as methyl alcohol, ethyl alcohol, isopropyl alcohol, butyl alcohol, cyclic ethers such as dioxane or tetrahydrofurane, aliphatic ethers, e.g. diethyl ether, dimethyl formamide, etc. as well as mixtures of these materials.

As protective groups for the amino group there can be used for example, the benzyl group, α-phenylethyl group, benzyl groups substituted in the benzene nucleus as for example, the p-bromo or p-nitrobenzyl group, the carbobenzoxy group, the carbobenzthio group, the trifluoroacetyl, the phthalyl radical, the trityl radical, the p-toluenesulfonyl radical and similar groups as well as simple acyl groups such as the acetyl group, formyl group, tert. butylcarboxy group, etc. There can be employed especially the protective groups used in the synthesis of peptides and the splitting processes customarily employed in that process. Among others for this purpose reference is made to Jesse P. Greenstein and Milton Winitz "Chemistry of Amino Acids", John Wiley and Sons, Inc. New York (1961) Vol. 2, pages 883 et seq. Also there can be used carbalkoxy groups (for example of low molecular weight such as carbmethoxy, carbethoxy and carbpropoxy).

Process (a) can also be carried out under some circumstances so that before the true cyclization there is isolated previously the intermediate product of the formula:

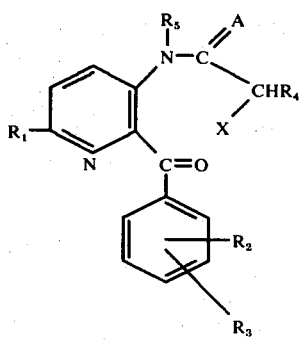

This product can then be cyclized in purified form or as it accumulates. For this purpose there are used temperatures between −70° and +150° C., preferably 0° to 150° C. As solvents or suspending media besides those given above there can be used glacial acetic acid, lower aliphatic alcohols such as methanol and ethanol, acetic anhydride, polyphosphoric acid, aliphatic ethers, e.g. diethyl ether, chloroform etc. This cyclization can be carried out in a given case using acid condensation agents such as sulfuric acid, hydrochloric acid, hydrobromic acid, toluene sulfonic acid or polyphosphoric acid or basic condensation agents such as pyridine or tertiary amines.

When X is a halogen atom the cyclization is carried out in the presence of ammonia (for example liquid ammonia), whereupon there can also be present teritary none quaternizing amines, for example, sterically hindered amines such as diisopropylethyl amine or 1,8-bis(dimethylamino) naphthalene. The halogen atoms employed are chlorine, bromine or iodine. In place of ammonia or additionally to ammonia there can also be used, for example, other derivatives of ammonia which replace a halogen atom by the group $NH_2$, for example, urotropine, alkaliamide e.g., sodamide, carboxylic acid amides, e.g., acetamide, alkali metal compounds of carboxylic acid amides or dicarboxylic acid imides. As dicarboxylic acid imides there can be used, for example, phthalimide or phthalimide substituted in the benzene nucleus with inert substituents, or succinimide. Besides there can be used acid radicals for the carboxylic acid amide which contain the above recited protective groups as well as protective groups customary in peptide chemistry. These types of protective groups are described for example among others in the book of Jesse P. Greenstein and Milton Winitz "Chemistry of Amino Acids", New York 1961, John Wiley & Sons, Inc., Vol. 2, for example, page 833 et seq.

When urotropine (hexamethylenetetramine) is used the process can be carried out as follows: boiling in chloroform (½ to 8 hours) and splitting off the separate urotropine compound with aqueous or aqueous-alcoholic inorganic acids (e.g., HCl or $H_2SO_4$) at temperatures between, for example, 20° and 150° C.

If acid amides are used it is recommended that there be used condensation agents such as sodium, alkali hydrides, e.g., sodium hydride, alkali amides (sepecially sodamides), Grignard compounds, lithium alkyls (e.g., butyl lithium) or in special cases, as with tosyl amides, there can be used weaker bases such as $K_2CO_3$, powdered NaOH or potassium hydroxide. As solvents above all dimethylsulfoxide and dimethyl formamide are suitable. There can also be used dioxane, tetrahydrofurane, alcohols, e.g., methyl alcohol, ethyl alcohol and isopropyl alcohol and ethers, e.g., diethyl ether. In using acid amides generally from the intermediate compound IV first there are obtained compounds of formula IV in which X is an amino group protected by the corresponding acid radical. The cyclization then takes place simultaneously with or after splitting off of the protective group. In acid splitting off of the protective group, it is generally possible to isolate the compounds of formula IV in which X is the amino group as either the salt or as the free base.

Where a starting material of formula II is used in process (a) in which $R_5$ is an acyl group this can be solvolytically split off in a given case after the end of the reaction according to the conditions mentioned previously. However, it is also possible, if a pure aliphatic acyl group is employed, to reduce this to an alkyl group (for example by means of complex alkali hydrides such as $LiAlH_4$).

It can happen that in the cyclization according to process (a) there is not formed the 7-membered ring compound but partially or exclusively the 6-membered ring compound of the formula:

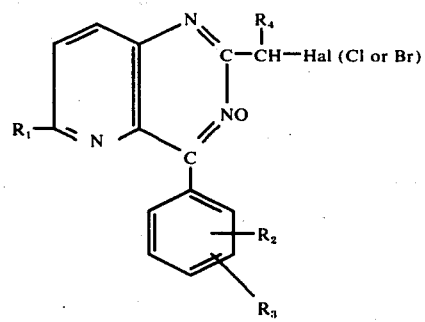

where Hal is chlorine or bromine. In this case a subsequent treatment in an alkaline medium is necessary. This is generally carried out in polar media such as lower alcohols (methanol, ethanol, tertiary butyl alcohol), chloroform, dioxane etc. at temperatures between 0° and 150° C. As the alkaline medium there can be used, for example, aqueous or alcoholic, especially methanolic or ethanolic NaOH or KOH, in a given case in admixture with the above mentioned solvents; the same reagents in solid, powdered form, also potash as well as aqueous solutions of tertiary amines, above all those which are not quarternized such as diisopropyl methyl amine. There can also be used alkaline ion exchanges, e.g., chloromethylated polystyrene quarternized with trimethylamine, in column form or in suspension.

In this ring expansion there are formed compounds in which the group $—N(R_5)C(=A)—$ in formula I has the following structure: $—N=C(OR_5)—$. In the ring expansion of compounds of formula V besides the desired diazepine often there are also formed compounds which are built from compounds of formula V without ring expansion by substitution of the halogen atoms by the particular coreactant. The desired compound can then be separated from this and, in a given case, other by-products also by fractional crystallization or by chromatography in known manner.

Process (b) is carried out for example in an inert solvent or suspension medium such as tetrahydrofurane, dioxane, ethanol, n-propanol, dimethyl sulfoxide or dimethyl formamide, or also in the presence of the basic reactant at a temperature between 50° and 200° C., preferably 80° to 130° C. There can be added acid acceptors such as potash, sodium bicarbonate, calcium carbonate or non-quarternizing tertiary amines such as diisopropylmethyl amines. To react the components of type $NHR_aAcyl$ the operation is carried out in the presence of alkali compounds such as sodium hydride, sodamide, butyl lithium, etc.; as solvents there can be used in this case those which contain no functional groups such as dioxane, dimethyl formamide or benzene. The temperatures are generally somewhat lower than those given above, for example, between 20° and 100° C.

According to process (c) azabenzodiazepines of formula I can be substituted or further reacted in suitable manner. The group A in a compound of formula I can also be exchanged in various ways.

Compounds of formula I wherein Z is a nitrogen atom can be converted into the corresponding N-oxide. Thus compounds of formula I in which Z is nitrogen can be reacted in inert solvents such as dilute acetic acid, ethyl acetate or acetone with hydrogen peroxide, peracetic acid, perpropionic acid, perbutyric acid, pervaleric acid, perbenzoic acid, m-chloroperbenzoic acid or other conventional organic peracids. The temperatures are preferably between 0° and 50° C. (otherwise at increase of temperature there occurs the above described rearrangement).

In compounds of formula I where Z is the group = NO the oxygen atom can be removed by catalytic hydrogenation, or by chemical deoxygenation. As catalysts for the catalytic hydrogenation there are suitable for example the customary metallic hydrogenation catalysts, especially noble metal catalysts (palladium-/activated carbon, platinum) or Raney-nickel; as solvents there are preferably employed lower alcohols, e.g., methanol, ethanol or isopropanol. The temperatures are between 0° and 200° C., preferably between 0° and 100° C. In a given case the process can be carried out at pressures up to 50 atmospheres absolute. For chemical deoxygenation there are preferably used phosphorus trichloride or dimethyl sulfoxide in inert solvents such as dioxane, benzene or toluene at temperatures between 0° and 150° C., preferably 0° to 100° C.

In the products of the process amino groups present including the nitrogen atom in the 1-position can be alkylated or quarternized by the radicals $R_a$, $R_b$, $R_c$ or $R_5$. For Example, compounds of formula I wherein $R_5$ and/or $R_1$ as well as $R_2$ are hydrogen or an amino group of the group $-NR_aH$ can be alkylated on the nitrogen in a manner known in itself. As alkylating agents can be used, for example, esters of the formula $R'_5$ Hal, Ar-$SO_2OR'_5$ and $SO_2(OR'_5)_2$ wherein Hal is a halogen atom (especially chlorine, bromine or iodine) and Ar is an aromatic radical as, for example, phenyl or naphthyl which in a given case is substituted by one or more lower alkyl groups and $R'_5$ with the exception of hydrogen can give the same meaning as $R_5$. Examples of compounds for example are p-toluene sulfonic acid alkyl esters, e.g., methyl p-toluene sulfonate, ethyl p-toluene sulfonate, butyl p-toluene sulfonate, lower dialkyl sulfates, e.g., dimethyl sulfate and diethyl sulfate and the like as well as alkyl halides, e.g., methyl iodide, ethyl iodide, butyl iodide, methyl bromide, ethyl chloride. The alkylation reaction can be carried out, in a given case with addition of customary acid binding agents such as alkali carbonates, e.g., sodium carbonate or potassium carbonate, pyridine or other customary tertiary amines, e.g., N,N-dimethyl aniline or triethyl amine, at temperatures between 0° and 150° C. in inert solvents such as alcohols, e.g., methyl alcohol, ethyl alcohol, isopropyl alcohol, propyl alcholol, dioxane, dimethyl formamide, dimethyl sulfoxide, aromatic hydrocarbons such as benzene or toluene or acetone as well as mixtures of such solvents. For the alkylation with alkyl halides (for example iodides) in the presence of NaH there has been found to be favorable for example, a mixture of toluene and a little dimethyl formamide (0.1 to 5%, for example, 0.5%).

In the alkylation it is also possible to proceed so that there is first produced from the reacting compound of formula I in which $R_4$ is H an alkali compound by reacting the compound of formula I with an alkali metal, alkali hydride or alkali amide (especially sodium or sodium compounds in an inert solvent such as dioxane, dimethyl formamide, benzene or toluene at temperatures between 0° and 150° C. and then to add the alkylating agent.

In place of the alkylation agents mentioned there can also be used other chemically equivalent agents (see, for example, L.F. and Mary Fieser "Reagents for Organic Synthesis", Vol. 2, page 471). Basic compounds of formula I can be converted into their salts by conventional methods. As anions for these salts there can be employed the known and therapeutically usable (pharmacologically acceptable) acid residues. For example, there can be used acids such as sulfuric acid, phosphoric acid, hydrohalic acids, e.g., hydrochloric acid or hydrobromic acid, ethylenediamine tetraacetic acid, sulfamic acid, benzene sulfonic acid, p-toluene sulfonic acid, camphor sulfonic acid, methane sulfonic acid, guarazulene sulfonic acid, maleic acid, fumaric acid, oxalic acid, tartaric acid, lactic acid, citric acid, ascorbic acid, glycolic acid, salicylic acid, acetic acid, propionic acid, gluconic acid, benzoic acid, acetamidoacetic acid, hydroxyethane sulfonic acid, malonic acid.

The free bases can be produced again from the salts of the compounds in customary manner, for example, by treatment of a solution in an organic medium, such as alcohols (e.g., methanol, ethanol or isopropanol) with soda or soda lye (caustic soda solution).

Compounds of formula I can also be present in tautomeric forms. Such tautomeric forms, for example, are the following structural pairs:

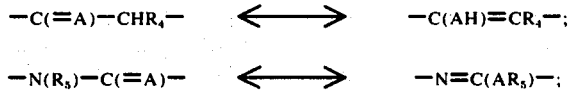

$-C(=A)-CHR_4- \longleftrightarrow -C(AH)=CR_4-$;

$-N(R_5)-C(=A)- \longleftrightarrow -N=C(AR_5)-$;

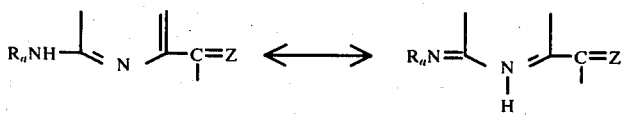

The compounds in this case can be present completely or partially in one of the possible tautomeric forms. Generally, under the normal working and storing conditions there is present an equilibrium.

Those compounds of formula I which contain asymmetric carbon atoms and as a rule result as racemates, can be split into the optically active isomers in known manner with the help of an optically active acid. However, it is also possible to employ from the beginning an optically active starting material whereby a correspondingly optically active or diastereomer form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, cremes, powders, liquids, dusts or aerosols. As liquids there can be used, for example, oily or aqueous solutions or suspensions, emulsions, injectable aqueous and oily solutions or suspensions.

For example, there can be made and used in the invention compounds of formula I where the symbols $R_1$ to $R_5$ as well as A and Z have the following meaning:

$R_1$ is $NH_2$, lower dialkylamino groups (e.g. alkyl groups of 1 to 3 carbon atoms such as dimethylamino, diethylamino, dipropylamino), morpholino, piperidino, hydroxyethylamino;

$R_2$ is chlorine, fluorine, $CF_3$, CN or alkyl with 1 to 3 carbon atoms, e.g., methyl, ethyl propyl or isopropyl, preferably methyl, preferably in the ortho or para position, hydrogen. The preferred substituents are hydrogen or fluorine or chlorine in the ortho position;

$R_3$ is hydrogen, fluorine or chlorine with the o-position being preferred;

$R_4$ is hydrogen;

$R_5$ is an alkyl or alkenyl group with 1 to 4 carbon atoms, e.g., methyl, ethyl, propyl, isopropyl, butyl, 5 butyl, allyl, methallyl, crotyl or butenyl-2 (preferably methyl, isopropyl, allyl or butenyl-2), or an aminoalkyl group with 2 to 4 carbon atoms, or mono or dialkylaminoalkyl of 2 to 4 carbon atoms, e.g., aminoethyl, aminopropyl, 4-aminobutyl, methylaminoethyl, dimethylaminoethyl or dibutylaminopropyl or diethylaminoisopropyl. Preferably $R_5$ is H or a lower alkyl group with 1 to 4 carbon atoms, for example, methyl;

A is oxygen or in the tautomeric form together with $R_5$, is $OR_5$ where $R'_5$ is a lower alkyl group, e.g., having 1 to 4 carbon atoms, especially methyl or ethyl;

Z is nitrogen or NO.

Especially favorable activity is possessed by compounds of formula I, where $R_1$ is dimethylamino, diethylamino, trimethylamino, morpholino or hydroxyethylamino, $R_2$ and $R_3$ are the same or different and are hydrogen, fluorine or chlorine, preferably in the ortho position, A is an oxygen atom and Z is a nitrogen atom, $R_4$ is hydrogen and $R_5$ is hydrogen or a lower alkyl group with 1 to 4 carbon atoms, especially the methyl group.

The starting compounds used in processes (a) and (b) insofar as they are not known can be obtained, for example, in the following manner:

Process (a).

A compound of the formula

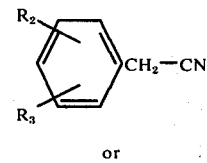

or

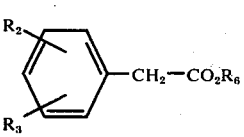

where $R_6$ is hydrogen or a lower alkyl group is first reacted with an active alkali compound such as sodamide, potassium amide, sodium hydride or sodium in finely divided form in an inert solvent such as dioxane, dimethyl formamide, or benzene and then there is added dropwise the calculated amount of 2,6-dichloro-3-nitropyridine dissolved in the same solvent with stirring and a nitrogen atmosphere. In many cases it is suitable to change the order of addition, for example, to add the alkali compound to a solution of the phenylacetic acid or benzyl cyanide derivative and 2,6-dichloro-3-nitropyridine. The generally exothermic reaction leads to the alkali salts of the compounds of formula VIII:

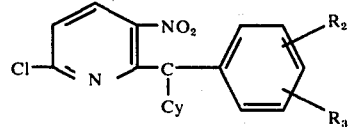

where Cy is CN or $CO_2R_6$ (where $R_6$ is H or lower alkyl). Such salts are colored strongly blue to violet.

After the end of the reaction this is filtered with suction, washed, dissolved in water and treated with diluted glacial acetic acid until the disappearance of the intrinsic color. The compound of formula VIII customarily crystallizes in sufficient purity.

The 2-[α-cyano-o-chlorobenzyl]-3-nitro-6-chloropyridine is recovered, for example, as follows:

To a solution of 120 grams of o-chlorobenzyl cyanide in 1.5 liters of dioxane there were added at 45° C. with stirring in a nitrogen atmosphere 42 grams of sodium hydride (80% in white oil). Then the mixture was stirred for 45 minutes more at this temperature. The solution was then cooled and at 20° to 22° C. there were dropped in within 30 minutes 140 grams of 2,6-dichloro-3-nitropyridine in 500 ml of dioxane. Further reaction was permitted for three hours at this temperature. The deeply colored sodium salt was filtered off, washed with dioxane, dissolved in water/methanol (1:1 by volume) and diluted acetic acid added until the color changed. The desired compound crystallized out, was filtered off with suction and thoroughly washed with methanol, M.P. 174°–175° C., Yield 91 grams.

By oxidation of the compound of formula VIII there can be produced the corresponding 2-benzoyl-3-nitro-6-chloropyridine derivative (formula IX):

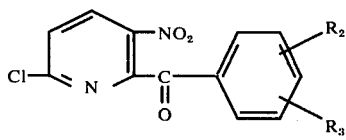
IX

This can be accomplished for example, with selenium dioxide in dioxane or tetrahydrofurane at 50° to 150° C. or can also be carried out by treating the compound of formula VIII with 30% aqueous hydrogen peroxide at temperatures below 100° C., preferably at 20° to 50° C. in acetone-water, wherein the stoichiometrical amount of an aqueous concentrated KOH solution is dropped in just rapidly enough that no change in color takes place. In the latter method there is simultaneously hydrolytically split off to a large extent the chlorine atom in the 6 position. There is also isolated therefore in addition to the desired compound of formula IX the compound wherein the 6-chloro atom is replaced by OH, i.e., $R_1$ is OH. The latter can then in known manner again be chlorinated with a mixture of $PCl_3/PCl_5$ wherein the $PCl_3$ simultaneously again deoxygenates the N-oxide formed as a byproduct.

In the compounds of formula IX the chlorine is replaced by the radical $R_1$ by reaction with $NH_3$ or amines of the form $NHR_aR_b$ in a solvent or suspension medium such as tetrahydrofurane or n-propanol at temperatures between 50° and 200° C. By reaction with a compound $R_cHal$ (Hal is bromine or iodine) under the conditions set forth above, quaternization can be accomplished. The nitro group is then reduced to an amino group either catalytically (with Pd, Pt or Raney-Ni in alcohol, dioxane or tetrahydrofurane between 0° and 60° C. and 1 to 50 atmospheres absolute) or chemically (with $LiAlH_4$ or $Al/Hg/H_2O$ in ether, dioxane or tetrahydrofurane between 0° to 60° C.). This amino group can then be substituted by the $R_5$ radical by the process given in the application. In this reduction in a given case further nitro groups (for example if $R_2$ and/or $R_3$ are nitro groups) can be reduced to amino groups. For the production of compounds of the formula X:

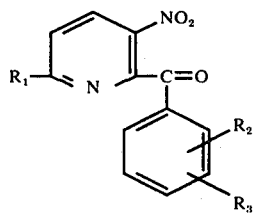
X where $R_1$ is F or Br for example, a compound of formula IX is heated with a saturated aqueous-alcoholic ammonia solution in an autoclave at 100° to 120° C. for several hours (e.g., 2 to 4 hours) and the 6-aminopyridine derivative formed thereby diazotised in known manner and reacted according to the conditions of the Sandmeyer reaction or the modified Sandmeyer reaction by heating in the presence of fluoride or bromide ions and/or the corresponding copper (I) salts (Cu Br, Cu Cl) or fluoroborate ions, e.g., sodium fluoroborate. As solvents there can be used water-alcohol mixtures, or mixtures of water, dimethyl formamide and dimethyl sulfoxide. For the production of fluorine derivatives there can also be employed the thermal decomposition of the dry diazonium fluoroborate.

Compounds of formula X in which $R_1$ is a bromine atom also can be obtained by bromination of the compound of formula X in which $R_1$ is replaced by OH by using a bromination agent such as $POBr_3$, $PBr_5$, or $SOBr_2$, in a given case in an inert medium between 20° and 200° C. The production of compounds of formula X wherein $R_1$ is F can also be produced in modified manner by either gradually adding $NaNO_2$ to a solution in aqueous hydrofluoric acid of a compound of formula X wherein $R_1$ is replaced by an amino group, at temperatures between 0° and 50° C., or by introducing a slow stream of nitrous gases to such a solution.

The reduction of the nitro group as well as the subsequent introduction of $R_5$ takes place in the manner already set forth.

The starting compounds used in process (b), e.g., can be prepared for example according to the process of Austrian Application No. 10604/71 or von Bebenburg et al U.S. application Ser. No. 313,542, filed Dec. 8, 1972 or in analogous manner to those processes. The entire disclosure of the von Bebenburg et al U.S. Application is hereby incorporated by reference. These starting compounds are claimed as new compounds in said von Bebenburg at al application.

Unless otherwise indicated, all parts and percentages are by weight.

EXAMPLE 1

5-phenyl-6-aza-7-dimethylamino-1,2-dihydro-3H-1,4-benzodiazepinone-(2):

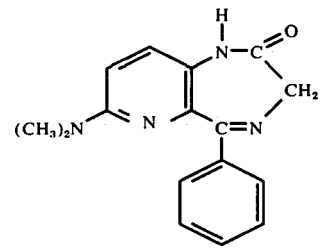

A mixture of 11 grams of 2-benzoyl-3-aminoacetylamino-6-dimethylaminopyridine, 1 ml of pyridine and 150 ml of toluene were boiled at reflux with stirring for 6 hours. The water which passed off was separated by means of a water separator. The desired substance began to crystallize out during the reaction. At the end of the reaction it was filtered off with suction and recrystallized from ethanol.

Yield 9.6 grams; M.P. 241° to 245° C. (with decomposition).

EXAMPLE 2

N-(5-phenyl-6-aza-1,2-dihydro-3H,-1,4-benzo-diazepinone-(2)-yl-(7))-N,N,N-trimethylammoniumiodide:

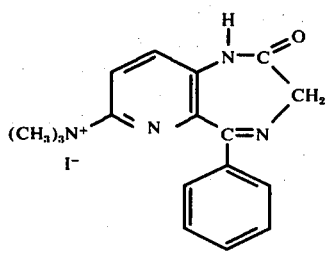

5 grams of 5-phenyl-6-aza-7-dimethylamino-1,2-dihydro-3H-benzo-1,4-diazepinone-(2) were boiled at reflux for 30 minutes in 100 ml of methyl iodide. The dark red crystals which crystallized out after cooling were recrystallized twice from n-propanol.

Yield 4 grams; M.P. 231° to 233° C. (with decomposition).

EXAMPLE 3

5-Phenyl-6-aza-7-morpholino-1,2-dihydro-3H-1,4-benzodiazepinone-(2):

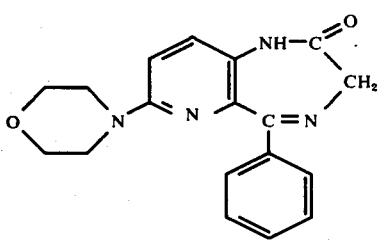

A mixture of 13.5 grams (0.05 mole) of 5-phenyl-6-azo-7-chloro-1,2-dihydro-3H-1,4-benzodiazepinone-(2) (prepared as described in example 1 of von Bebenburg application 313,542) and 50 ml of water free morpholine were held for 1 hour at 130° C. with stirring. Then the mixture was cooled, poured on ice and after 1 hour the precipitated solid substance filtered off with suction. It was dissolved in chloroform, the chloroform solution shaken with 200 ml of 2% hydrochloric acid and the aqueous layer separated off. Then it was neutralized with aqueous ammonia with cooling, whereby the desired product crystallized out.

Yield 10 grams; M.P. 265° to 270° C.

EXAMPLE 4

5-(o-fluoro-phenyl)-6-aza-7-morpholino-1,2-dihydro-3H-1,4-benzodiazepinone-(2):

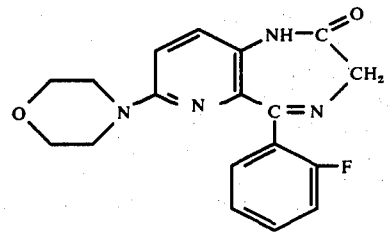

A mixture of 10 grams of 5(o-fluorophenyl)-6-aza-7-chloro-1,2-dihydro-3H-1,4- benzadiazepinone-(2) (prepared as described in example 10 of von Bebenburg application 313,542) and 50 ml of water free morpholine were heated to 130° C. for 1 hour with stirring. After cooling the mixture was poured on ice and after one hour the precipitated material was filtered off with suction. This material was then dissolved in chloroform and then shaken with 200 ml of 2% HCl and the aqueous phase neutralized with dilute ammonia with cooling. The desired product crystallized out (4 grams) from the aqueous solution and was recrystallized from a little ethanol with the addition of gasoline. M.P. 227° to 240° C.

EXAMPLE 5

5-phenyl-6-aza-7-(2-hydroxy-ethylamino)-1,2-dihydro-3H-1,4-benzodiazepinone-(2):

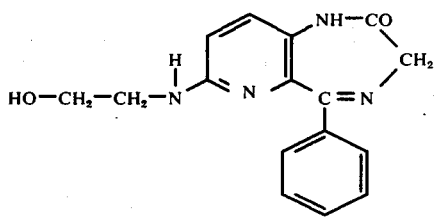

A mixture of 13.5 grams (0.05 mole) of 5-phenyl-6-aza-7-chloro-1,2-dihydro-3H-1,4-benzodiazepinone-(2) and 50 ml of dry ethanolamine were stirred for one hour at 100° C., then poured on ice and extracted with 100 ml of ether. The ether layer was washed several times with water, dried and then the hydrochloride of the desired compound was precipitated with isopropanolic HCl. This crystallized upon rubbing, was filtered off with suction and recrystallized from n-propanol.

Yield 5 grams; M.P. 210° to 215° C.

EXAMPLE 6

5-(o-chlorophenyl)-6-aza-7-benzylamino-1,2-dihydro-3H-1,4-benzodiazepinone-(2);

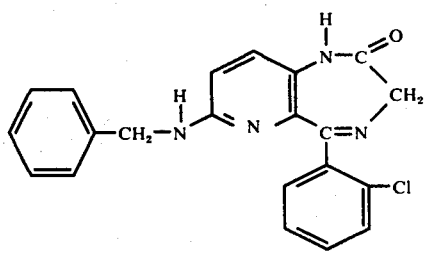

A mixture of 20 grams of 2-(o-chlorobenzoyl-3-(bromoacetamino)-6-benzylaminopyridine, 400 gram of methanol and 65 grams of ammonia were heated in the autoclave for 90 minutes at 80° C. The autoclaved solution was then concentrated to 200 ml, treated with 1 liter of water, decanted off from the separated amorphous substance and the amorphous substance recrystallized from benzene.

M.P. 195°–197° C.

EXAMPLE 7

5-(o-chlorophenyl)-6-aza-7-dimethylamino-1,2-dihydro-3H-1,4-benzodiazepinone-(2);

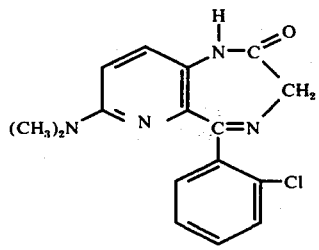

A mixture of 14 grams of 2-(o-chlorobenzoyl)-3-amino-6-dimethylamino pyridine, 15 rams of glycine methyl ester hydrochloride and 15 grams of imidazole were melted and stirred for 90 minutes at 110° to 120° C. The melt was diluted with a little methanol and poured into 200 ml of water. The separated oil was isolated and dissolved in 100 ml of hot toluene. The material crystallized out of the solution upon cooling. It was recrystallized once more from ethanol.

M.P. 242 to 243° C.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers and assistants as set forth for example are those recommended in the following literature as adjuvants for pharmacy, cosmetic and related fields such as in Ullmann's Encyklopadie der technischer Chemie, Vol. 4 (1953), pages 1 to 39; Journal of Pharmaceutical Sciences, Vol. 52 (1963), pages 918 et seq.; H. v. Czetsch-Lindenwald, Hilfstoffe fur Pharmazie und angrenzende Gebiete; Pharm. Ind. Vol. 2 (1961), pages 72 et seq.; Dr. H.P. Fiedler, Lexicon der Hilfstoffe fur Pharmazie, Kosmetik und angrenzende Gebiete, Cantor Kg. Aulendorf i. Wurtt, 1971.

Examples of such materials include gelatin, natural sugars such as sucrose or lactose, lecithin, pectin, starch (for example corn starch), tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols, (for example, methyl hydroxypropyl cellulose, methyl cellulose, hydroxyethyl cellulose), stearates, e.g., methylstearate, and glyceryl stearate, magnesium and calcium salts of fatty acids with 12 to 22 carbon atoms, especially saturated acids (for example calcium stearate, calcium laurate, magnesium oleates, calcium palmitate, calcium behenate and magnesium stearate), emulsifiers, oils and fats, especially of plant origin (for example, peanut oil, castor oil, olive oil, sesame oil, cottonseed oil, corn oil, mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, glycol furfural, dimethyl acetamide, lactamide, lactates, e.g, ethyl lactate, ethyl carbonate, silicones (especially middle viscosity dimethyl polysiloxane) and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g, stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic diacetin, glyceryl monostearate, glyceryl distearate, glyceryl monopalmitate, paraffins and the like.

In the production of the preparations there can be used known and conventional solvent aids. As solvent aids there can be used, for example, polyoxyethylated fats, e.g., polyoxyethylated oleo triglyceride, linolized oleotriglyceride. Examples of oleotriglycerides are olive oil, peanut oil, castor oil, sesame oil, cottonseed oil, corn oil (see also Dr. H. P. Fielder, "Lexikon der Hilfsstoffe fur Pharmazie, Kosmetik und angrenzende Gebiete", 1971, pages 191 to 195.

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Furthermore, there can be added preservatives, stabilizers, buffers, taste correctives, antioxidants and complex formers (for example ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydroguararetic acid, tocopherols such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester benzoic acid), sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The drugs can be used for example orally, parenterally, rectally, vaginally, perlingually or locally.

It is also possible to add other medicines.

The compounds of the invention have a good anticonvulsive activity and anxiolytic activity respectively in the cardiazole shock test (mouse) and the spasmolytic test according to Tedeschi (mouse).

This activity is comparable to the activity of known medicines Diazepam and Medazepam.

The lowest effective dosage in the above-mentioned animal experiments is for example 5 mg/kg body weight orally, 0.5 mg/kg body weight intraveneously and 1 mg/kg sublinqually.

As general dosage ranges there can be used 5 to 100 mg/kg body weight orally, 0.5 to 10 mg/kg body weight intravenously and 1–20 mg/kg sublinqually.

The compounds of the invention can be used in treatment of excitement, stress, anxiety, increased irritability, psychoneurotic disturbances of children, vegetative dystony, psychosomatic disturbances and organic neuroses, sleep disturbances, muscle spasms (as well as illnesses of the rheumatic series) and treatment of spasms. They also are useful for making birth easier, Abortus imminens, treating threatened and beginning premature or delayed birth. Placenta praevia and in preparation for operation.

The pharmaceutical preparations generally contain between 0.5 and 5% mg of the active component (or components) of the invention.

The compounds can be delivered in the form of tablets, capsules, pills, dragees, suppositories, salves, gels, creams, powders, liquids, dusts or aerosols. As liquids there can be used oily or aqueous solutions or suspensions, emulsions. The preferred forms of use are the tablets which contain between 5 and 100 mg of active material or solutions which contain between 1 and 10% of active material.

In individual doses the amount of active component of the invention can be used for example in an amount of:
 a. in oral dispensation between 5 and 150 mg;
 b. in parenteral dispensation (for example intravenously, intramuscularly) between 0.5 and 10 mg;
 c. in inhalation dispensation (solutions or aerosols) between 1 and 20 mg;
 d. in rectal or vaginal dispensation between 5 and 150 mg (The dosages in each case are based on the free base).

For example, there is recommended the use of 1 to 3 tablets containing 1 to 100 mg of active ingredient 3 times daily or for example, intravenously the injection 1 to 3 times daily of a 0.5 to 2 ml ampoule containing 0.5 to 10 mg of active substance. In oral preparations the minimum daily dosage for example is 10 mg; the maximum daily dosage should not be over 1000 mg.

In the treatment of dogs and cats the oral individual dosage in general is between about 5 and 100 mg/kg body weight; the parenteral individual dosage is between about 0.5 and 10 mg/kg body weight. In the treatment of horses and cattle the individual dosage orally is generally between 5 and 500 mg/kg; the parenteral individual dosage is between 0.5 and 50 mg/kg body weight.

The acute toxicity of the compounds of the invention in the mouse (expressed by the $LD_{50}$ mg/kg method of Miller and Tainter, Proc. Soc. Exper. Biol. and Med., Vol. 57 (1944), pages 261 et seq.) in oral application is between 500 mg/kg and 2000 mg/kg (or above 2000 mg/kg).

The drugs can be used in human medicine, in veterinary medicine, e.g., to treat cats, dogs, horse, sheep, cattle, goats and pigs or in agriculture. The drugs can be used alone or in admixture with other pharmacologically active materials.

The salts can also be used as curing agents for melamine-formaldehyde resins.

EXAMPLE 8

1-methyl-5-(o-chlorophenyl)-6-aza-7-dimethylamino-1,2-dihydro-3H-1,4-benzodiazepinone-(2).

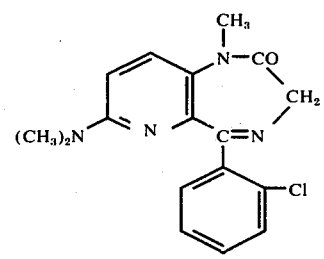

To a solution of 6 grams of 5-(o-chlorophenyl)-6-aza-7-dimethylamino-1,2-dihydro-3H-1,4-diazepinone-(2) (prepared in Example 7) in 50 ml of dry dimethyl formamide there was added with stirring in a nitrogen atmosphere at room temperature 0.9 gram of sodium hydride (57% in white oil) and the mixture allowed to stir for one hour whereupon the temperature rose to 49° C. Then there were added dropwise 3 grams of methyl iodide whereupon the temperature rose to 50° C. The mixture was stirred for 2 hours and then 200 ml of water were added. The oil which precipitated crystallized upon rubbing and standing. The material was recrystallized from a little methanol. M.P. 158°–162° C.

EXAMPLE 9

1-allyl- 5-(o-chlorophenyl)-6-aza-7-dimethylamino-1,2-dihydro-3H-1,4-benzodiazepinone-(2).

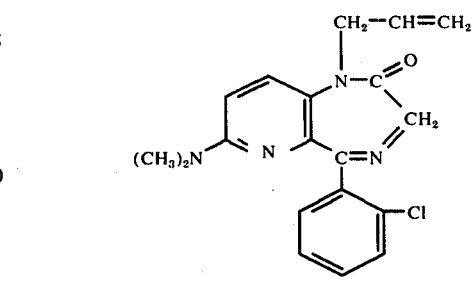

The procedure of Example 8 was repeated replacing the methyl iodide by 3 grams of allyl bromide to obtain the title compound. M.P. 113°–115° C.

Starting materials for EXAMPLE 1 a. 2-benzoyl-3-nitro-6-dimethylaminopyridine. 124 rams of 2-benzoyl-3-nitro-6-chloropyridine (prepared acc. to U.S. application Ser. No. 313,542) were dissolved in 500 ml n-propanol and 50 grams dimethylamine were introduced into the solution at 100° C with stirring within 3 hours. Stirring was then continued for 1 hour and the solution left over night. The desired compound crystallized out on seeding. It was filtered with suction and washed with ethanol.

Yield 114 grams; M.P. 115° to 117° C.

b. 2-benzoyl-3-amino-6-dimethylaminopyridine. 50 grams of the above nitro-compound were dissolved in 500 ml methanol and 20 grams hydrazine-hydrate were added. Then 5 grams Raney nickel were added in portions with stirring at 30° C within 90 minutes. After standing over night the mixture was filtered, the filtrate concentrated in vacuo, and the remainder dissolved in 500 ml chloroform and chromotographed over silica gel. The eluate was evaporated, the remaining sirup crystallized slowly. It was used for further reaction without further purification.

Yield 24 grams.

c. 2-benzoyl-3-carbobenzoxyaminoacetylamino-6-dimethylaminopyridine.

A mixture of 22 grams of the compound obtained under (b), 22 grams carbobenzoxyglycine, 200 ml of dioxane and 22 grams of ethyl-1,2-dihydro-2-ethoxy-1-quinolinecarboxylate (EEDQ) were stirred at room temperature for 90 minutes. To the resulting solution then ether and petroleumether were added to turbidity. The compound crystallized on seeding.

Yield 20 grams; M.P. 114° C.

d. 2-benzoyl-3-aminoacetylamino-6-dimethylaminopyridine.

19 grams of the compound obtained under (c) were added in portions to 150 ml of a 40% solution of HBr in acetic acid at room temperature with stirring, whereby carbondioxide was evolved. After the addition the solution was left for 1 hour, then diluted with 600 ml of ether with stirring. The precipitate crystallized on prolonged stirring. It was filtered with suction, dissolved in 50 ml of methanol, made alkaline with aqueous ammonia and diluted with water until turbid. The resulting crystals were filtered with suction. Yield 11 grams. On melting the compound partly cyclized to the compound acc. to example 1.

Starting materials for EXAMPLE 6 a. 2-(o-chlorobenzoyl-)-3-nitro-6-dimethylaminopyridine.

100 grams of 2-(o-chlorobenzoyl-)-3-nitro-6-chloropyridine (prepared acc. to U.S. application Ser. No. 313,542) were reacted as described above for starting materials of example 1.

Yield 90 grams; M.P. 142° C.

b. 2-(o-chlorobenzoyl-)-3-amino-6-dimethylaminopyridine.

The reduction of (a) was carried out as shown under starting material for example 1 with hydrazine and Raney nickel. 30 grams of the nitro compounds gave 17 grams of the sirupy amine.

Starting materials for EXAMPLE 7 a. 2-(o-chlorobenzoyl-)-3-nitro-6-benzylaminopyridine. A mixture of 52.5 grams of 2-benzoyl-3-nitro-6-chlorpyridine, 300 ml n-propanol, 23.5 grams benzylamine and 28 grams potassium carbonate was stirred with reflux for 5 hours. The hot solution was filtered. The product crystallized on cooling. It was filtered with suction and washed with n-propanol.

Yield 44.5 grams; M.P. 140° to 143° C.

b. 2-(o-chlorobenzoyl-3-amino-6-benzylaminopyridine. The nitro compound described above was reduced with hydrazine and Raney nickel in the manner shown under starting materials for example 1. The compound crystallized after chromatographing. 45 grams of the nitro compound yielded 28 grams of the amino compound. M.P. 130° C.

c. 2-(o-chlorobenzoyl-)-3-(bromacetamino-)-6-benzylaminopyridine 23 grams of the 3-amino compound were suspended in 200 ml of dioxane and 10 ml of pyridine. Then 13 grams of bromoacetylbromide were added in portions with stirring. The temperature rose to 50° C and a clear solution resulted. Stirring was continued for 30 minutes, then the mixture was poured on 750 ml of ice water. The precipitating oil was dissolved in 200 ml of ether, and ether solution dried and an ethanolic solution of HCl added. The precipitating sirup crystallized on seeding. The crystals were filtered off and recrystalized from n-propanol.

Yield 20 grams; M.P. 149° to 151° C.

EXAMPLE 10

5-phenyl-6-aza-7-amino-1,2-dihydro-3H-1,4-benzodiazepinone-(2)

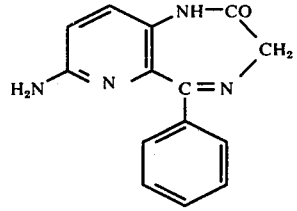

A melt of 80 grams of glycine methyl ester hydrochloride, 59 grams of 2-benzoyl-3,6-diaminopyridine and 100 grams of imidazole were heated at 110°–115° C. for 30 minutes. Initially the mixture was stirred, after about 10 minutes the melt solidified. The solid cake was triturated with 60 ml. of methanol, filtered with suction, the filtrate concentrated to 200 ml. and poured into 1 liter of water. The product which crystallized out was filtered off with suction and recrystallized from methanol. Yield 41 grams; M.P. 242°–244° C.

The starting material for Example 10 was obtained as follows:

A solution of 180 grams of 2-benzoyl-3-nitro-6chloropyridine and 80 grams of ammonia in 1 liter of alcohol was heated at 100°–120° C. for 5 hours in an autoclave. The reaction solution was evaporated to dryness, the residue thoroughly stirred with 1.5 liters of acetone and filtered. Therewere added 100 ml. of concentrated hydrochloric acid and 3 liters of water, the crystallized reaction products, the 2-benzoyl-3-nitro-6-aminopyridine, was washed with water. Yield 161 grams; M.P. 196°–198° C.

153 grams of 2-benzoyl-3-nitro-6-aminopyridine were hydrogenated in 900 ml. of dioxane with 20 grams of Raney nickel at 40 atmospheres absolute and 60°–70° C. The product was separated from the catalyst by filtering with suction and the filtrate treated with 6N ethanolic hydrochloric acid. The crystallized 2-benzoyl-3,6-diaminopyridine hydrochloride formed was filtered off with suction and washed with acetone. It was dissolved in some water, made alkaline with aqueous sodium hydroxide whereupon the base first separated out as an oil and later crystallized. It was filtered off with suction and recrystallized from ethanol. Yield 84 grams; M.P. 100°–102° C.

EXAMPLE 11

1-[1-dimethylaminoethyl-(2)]-5-(o-chlorophenyl)-6-aza-7-dimethylamino-1,2-dihydro-3H-1,4-benzodiazepinone-(2)

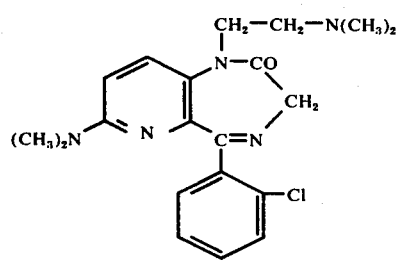

To a solution of 32 grams of 5-(o-chlorophenyl)-6-aza-7-dimethylamino-1,2-dihydro-3H-1,4-benzodiazepinone-(2) in 200 ml. of dry dimethyl formamide there were added with stirring 3.3 grams of sodium hydride (80% in white oil) and allowed to react for 30 minutes. The mixture was then heated to 70° C. and there were added 20 grams of freshly produced dimethylaminoethyl chloride (base) in a little dimethyl formamide. Then the mixture was heated to 100° C. and stirred for 30 minutes. The solution was filtered, then there were added 6N isopropanolic hydrochloric acid up to an acid reaction and 700 ml. of ether. The top layer was decanted from the precipitated syrup, the syrup washed with acetone and dissolved in a little water. The solution was made ammoniacal, whereupon the base first precipitated as an oil and after some time crystallized. It was recrystallized from methylene chloride-cyclohexane (: by volume). Yield 12 grams; M.P. 119°–120° C.

EXAMPLE 12

5-phenyl-6-aza-7-(N'-methylpiperazino)-1,2-dihydro-3H-1,4-benzodiazepinone-(2)

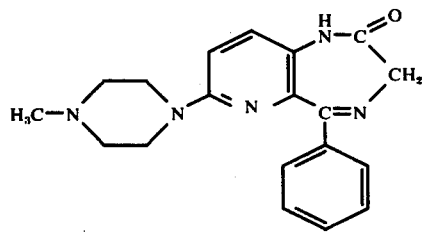

A mixture of 10 grams of 5-phenyl-6aza-7-chloro-1,2-dihydro-3H-1,4-benzodiazepinone-(2) and 100 ml. of N-methylpiperazine were heated for 2 hours under reflux. The solution was then evaporated to dryness in a vacuum, the residue dissolved in chloroform, washed with some water, then the solution dried and gasoline added until turbidity was observed. The material then crystallized upon rubbing. It was recrystallized from ethanol with addition of activated carbon. Yield 3.5 grams; M.P. 226°–228° C.

EXAMPLE 13

5-(o-chlorophenyl)-6-aza-7-pyrrolidino-1,2-dihydro-3H-1,4-benzodiazepinone-(2)

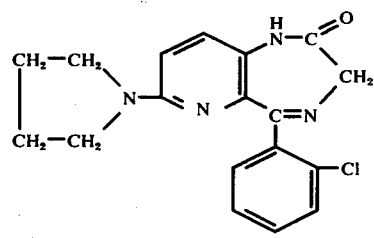

A mixture of 10 grams of 5-(o-chlorophenyl)-6-aza-7-chloro-1,2-dihydro-3H-1,4-benzodiazepinone-(2) and 15 ml. of pyrrolidine were heated at reflux for 1 hour. The solution was evaporated to dryness in a vacuum, the residue dissolved in chloroform, washed with some water, then the solution dried and gasoline was added until turbidity. The substance crystallized upon rubbing. It was recrystallized from ethanol with addition of activated carbon. Yield 6 grams; M.P. 158°–160° C.

EXAMPLE 14

Example of an Acid Addition Salt

The compound prepared in Example 7 was dissolved in a little acetone, then isopropanolic hydrochloric acid solution was added until an acid reaction, whereupon the hydrochloride crystallized out. It was filtered off with suction, the yield was nearly quantitative, M.P. above 300° C.

What is claimed is:

1. A 6-aza-3H-1,4-benzodiazepine or 6-aza-1,2-dihydro-3H-1,4-benzodiazepine of the formula:

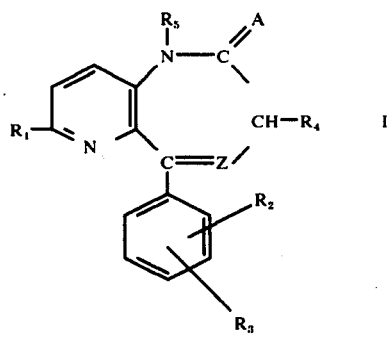

wherein:

$R_1$ is the group $-NR_aR_b$ or $N^+R_aR_bR_cX^-$ where $R_a$ and $R_b$, are hydrogen, alkyl groups of 1 to 6 carbon atoms, benzyl, or alkyl groups of 1 to 6 carbon atoms substituted by a single hydroxy, and $R_c$ is alkyl of 1 to 6 carbon atoms with the proviso that when $R_c$ is present $R_a$ and $R_b$ are both alkyl of 1 to 6 carbon atoms and wherein the group $-NR_aR_b$ also can be morpholino, pyrrolidino, piperidino, homopiperidino, piperazino or N-alkyl piperazino having 1 to 6 carbon atoms in the alkyl group; $X^-$ is a halide, sulfate, acetate, citrate or p-toluene sulfonate;

$R_2$ and $R_3$ are hydrogen, halogen, trifluoromethyl, nitro, nitrile, hydroxy, lower alkyl or lower alkoxy;

$R_4$ is hydrogen;

Z is a nitrogen atom or the NO group;

$R_5$ is hydrogen, lower alkyl, lower alkenyl, aminoalkyl of 2 to 4 carbon atoms, mono or di lower alkyl substituted aminoalkyl of 2 to 4 carbon atoms; and A is oxygen, and compounds where the $-N(R_5)-C(=A)$ group in formula I is replaced by the tautomeric form $-N=C(AR_5)$, and pharmaceutically acceptable salts and quarternary ammonium and alkyl ammonium compounds thereof.

2. A compound according to claim 1 wherein when $R_2$ or $R_3$ is halogen the halogen is fluorine, bromine or chlorine.

3. A compound according to claim 2 wherein $R_1$ is alkylamino of 1 to 6 carbon atoms, a dialkylamino with 1 to 6 carbon atoms in each alkyl group, hydroxyalkylamino having 2 to 4 carbon atoms, benzylamino, morpholino, pyrrolidino, piperidino, piperazino, N-alkylpiperazino having 1 to 6 carbon atoms in the alkyl group, or homopiperidino or $R_1$ is further quarternized with an alkyl of 1 to 3 carbon atoms, $R_2$ and $R_3$ are hydrogen, fluorine, chlorine or bromine, $R_4$ is hydrogen, $R_5$ is hydrogen or alkyl of 1 to 6 carbon atoms, and A is oxygen.

4. A compound according to claim 3 wherein $R_3$ is hydrogen.

5. A compound according to claim 4 wherein when an alkyl group is present it has up to 4 carbon atoms.

6. A compound according to claim 5 wherein when an alkyl group is present it is methyl.

7. A compound according to claim 5 wherein $R_1$ is dialkylamino, trialkylamino halide, morpholino, hydroxyethylamino, benzyl, amino, N-methylpiperazino or pyrrolidino, $R_2$ is hydrogen, chlorine or fluorine, $R_4$ is hydrogen, $R_5$ is hydrogen and A is oxygen.

8. A compound according to claim 2 wherein $R_1$ is amino, dialkylamino, trialkylamino halide, hydroxyalkylamino of 1 to 6 carbon atoms, benzylamino, N-alkyl piperazino or morpholino, $R_2$ is hydrogen, halogen, $R_3$ is hydrogen, $R_5$ is hydrogen, lower alkyl, lower alkenyl or di lower alkyl aminoalkyl and A is oxygen.

9. A composition having psychosedative or anxiety relieving activity comprising an effective amount for such activity of a compound of claim 2 in a pharmaceutically acceptable carrier.

10. A method of inducing a psychosedative or anxiety relieving effect in a mammal comprising administering to the mammal an amount of the compound of claim 1 sufficient to induce such effect.

11. A method according to claim 10 wherein the compound is administered orally.

12. A method according to claim 10 wherein the compound is administered intravenously.

* * * * *

UNITED STATES PATENT OFFICE
CERTIFICATE OF CORRECTION

Patent No. 4,009,271  Dated February 22, 1977

Inventor(s) Walter von Bebenburg and Heribert Offermanns

It is certified that error appears in the above-identified patent and that said Letters Patent are hereby corrected as shown below:

[30]     Foreign Application Priority Data

April 27, 1973          Austria ................. A3772/73

Signed and Sealed this

Twenty-sixth Day of April 1977

[SEAL]

Attest:

RUTH C. MASON  
Attesting Officer

C. MARSHALL DANN  
Commissioner of Patents and Trademarks